US008203255B2

(12) United States Patent
Loschonsky et al.

(10) Patent No.: US 8,203,255 B2
(45) Date of Patent: Jun. 19, 2012

(54) PIEZOELECTRIC SENSOR ARRANGEMENT COMPRISING A THIN LAYER SHEAR WAVE RESONATOR BASED ON EPITACTICALLY GROWN PIEZOELECTRIC LAYERS

(75) Inventors: Marc Loschonsky, Freiburg (DE); Armin Dadgar, Berlin (DE); Leonhard Reindl, Freiburg (DE)

(73) Assignee: Albert-Ludwigs-Universitat Freiburg, Freiburg (DE)

( * ) Notice: Subject to any disclaimer, the term of this patent is extended or adjusted under 35 U.S.C. 154(b) by 0 days.

(21) Appl. No.: 12/518,054

(22) PCT Filed: Dec. 5, 2007

(86) PCT No.: PCT/EP2007/010571
§ 371 (c)(1),
(2), (4) Date: Oct. 13, 2009

(87) PCT Pub. No.: WO2008/068011
PCT Pub. Date: Jun. 12, 2008

(65) Prior Publication Data
US 2010/0127600 A1    May 27, 2010

(30) Foreign Application Priority Data
Dec. 7, 2006  (DE) .......................... 10 2006 057 730

(51) Int. Cl.
*H01L 41/04* (2006.01)
(52) U.S. Cl. ........................................ 310/338; 310/346
(58) Field of Classification Search .................. 310/338, 310/346
See application file for complete search history.

(56) References Cited

U.S. PATENT DOCUMENTS

| 7,148,611 | B1* | 12/2006 | Liu | 310/366 |
|---|---|---|---|---|
| 2004/0135144 | A1* | 7/2004 | Yamada et al. | 257/59 |
| 2004/0187580 | A1* | 9/2004 | Nozaki | 73/580 |
| 2005/0189846 | A1* | 9/2005 | Saito et al. | 310/311 |
| 2007/0000305 | A1* | 1/2007 | Ma et al. | 73/24.01 |
| 2007/0194347 | A1* | 8/2007 | Kikkawa | 257/194 |
| 2009/0079442 | A1* | 3/2009 | Gabl et al. | 324/663 |

FOREIGN PATENT DOCUMENTS

| DE | 10308975 A1 | 2/2004 |
|---|---|---|
| DE | 102004002914 A1 | 8/2005 |
| DE | 1020060557730 A1 | 12/2007 |

(Continued)

OTHER PUBLICATIONS

Machine translation of WO 2006/034906 provided by the website of the European Patent Office.*

(Continued)

*Primary Examiner* — Derek Rosenau
(74) *Attorney, Agent, or Firm* — Michael Best & Friedrich LLP

(57) ABSTRACT

The invention relates to piezoelectric sensor arrangements, especially sensor arrangements that can be operated in a measuring fluid, in order to be able to detect, for example, elastic properties of the measuring fluid itself or the presence and/or concentration of analyte molecules in the fluid. According to the invention, the sensor arrangement comprises an acoustic resonator which has a sensitive region and is arranged such that a resonance frequency of the sensor arrangement varies according to properties of the measuring fluid. The acoustic resonator is formed by a piezoelectric thin layer resonator and the sensitive region is produced by means of epitaxy, such that transversally polarized vibration modes can be induced.

12 Claims, 1 Drawing Sheet

FOREIGN PATENT DOCUMENTS

WO 2004/055982 A1 7/2004
WO WO 2006/034906 * 4/2006
WO 2006/101450 A1 9/2006

OTHER PUBLICATIONS

International Search Report for Application No. PCT/EP2007/010571 dated Apr. 22, 2008 (3 pages).

International Preliminary Report on Patentability with Written Opinion (translated) for Application No. PCT/EP2007/010571 dated Jul. 7, 2009 (10 pages).

Bjurstrom J. et al., "Synthesis of textured thin piezoelectric AlN films with a nonzero c-axis mean tilt for the fabrication of shear mode resonators", Ultrasonics symposium, 2005, Ieee Rotterdam, The Netherlands, Sep. 18-21, 2005, Piscataway, NJ, USA, IEEE, pp. 321-324, XP010898904, ISBN 0-7803-9382-1.

German Office Action for Application No. 102006057730.2 dated Dec. 7, 2006 (3 pages).

German Office Action for Application No. 102006057730.2 dated Jul. 23, 2008 (3 pages).

* cited by examiner

PIEZOELECTRIC SENSOR ARRANGEMENT COMPRISING A THIN LAYER SHEAR WAVE RESONATOR BASED ON EPITACTICALLY GROWN PIEZOELECTRIC LAYERS

BACKGROUND

The present invention relates to piezoelectric sensor arrangements, in particular to sensor arrangements, which can be operated in a measuring fluid in order to detect for example the elastic properties of the measuring fluid itself or the presence and/or the concentration of the analyte molecules in the fluid.

SUMMARY

The requirements for the measurement resolution of the smallest amounts of substances have increased enormously in the last years, for process technologies, medical and chemical-biological problems. For these problems there already exist well-developed measurement techniques and equipment (such as for example the atomic force and electron microscope and mass spectroscopy) which require specially equipped laboratories, but there is a lack of portability and low-cost as well as simple to use and manageable solutions. Use of such miniaturized measuring systems allow, for example, security staff using this on-site to simply detect the smallest substance amounts (such as dynamite or narcotics). Such a system can equally be used for a direct proof of substances in the medical or chemical-biological sectors (e. g. pathogenic germs, viruses or proteins). In process technology the scatter of the process could be decreased, which was previously controlled with the help of a quartz crystal microbalancing process.

For this purpose over many years quartz crystal microbalances have been used (*Use of Quartz crystal oscillators for weighing thin films and for micro-weighing*, G. Sauerbrey, Zeitschrift fuer Physik 155, 206-222 (1959)), with which an accumulated amount of substance $\Delta m$ is transformed into a frequency shift $\Delta f$, according to Sauerbrey's equation:

$$\frac{\Delta f}{f} = -\frac{\Delta m}{m} \tag{1}$$

The mass resolution $\Delta m$ of the quartz crystal microbalance results from the extremely high quality factor of the quartz crystal, which allows a detectable frequency shift $\Delta f$ of 25 Hz. In fundamental oscillation mode, the quartz thickness equates to a half acoustical wavelength. On the upper- and under-side of the quartz plate a total reflection occurs, due to an impedance jump. The process-specific thickness of the quartz plate of around 50 μm limits the resonant frequency f of the fundamental mode from typically 10 Mhz up to a maximum of 55 MHz. Quartz crystal microbalances within this frequency range have been successfully made and distributed by a few manufacturers, since the middle of the 1970's. Should the selected electrode diameter be too small, then parasitic higher-order modes dominate and the stability of the oscillator is lost. Both of these aspects limit the minimum mass m of the acoustic resonator. Together with the electronic noise as well as the remaining system errors, there results a maximum mass resolution of a few picograms.

The use of surface acoustic wave components (SAW) as mass sensitive resonators in principle offers the opportunity to increase the resonant frequency f and to substantially decrease the oscillating mass m. The resonant frequency of the SAW resonator is defined by the cycle period of the finger structure, currently in the range from 50 MHz to 3.15 GHz. The total reflection occurs due to acoustical Bragg gratings which are provided on both sides. A mass absorption changes the properties of the SAW through a second-order effect (so-called "mass and stressloading"). The attainable quality factor of SAW resonators of maximum 10,000 lies significantly under that of quartz resonators. Both of these effects decrease the sensitivity of the SAW microbalance with respect to quartz crystal micro balances. Microbalances based upon SAW resonators are currently still in the research and development stadium with only a limited field of application, as described for instance in: *SAW and QMB for Chemical Sensing*, F. L. Dickert, P. Forth, M. Tortschanoff, W. Bulst, G. Fischerauer, U. Knauer, IEEE International Frequency Control Symposium, 120-123 (1997).

The rapid advances of mobile telecommunications led to a dramatic increase in demand for high frequency, steep-edged, miniaturised filter components. For this purpose currently surface acoustic wave based filters and most-recently also acoustic thin film resonators (so-called FBARs—Thin Film Bulk Acoustic Resonators) have been utilised. [see e. g. *Face-mounted piezoelectric resonators*, W. E. Newell, Proceedings of the IEEE, vol. 53, 575-581, (1965), or *Thin Film Resonator Technology*, K. M. Lakin—IEEE transactors on Ultrasonics, Ferroelectrics, and Frequency Control, vol. 52, no. 5, 707-716 (2005)]. The FBARs are based upon the "Bulk Acoustic Wave"-principle (BAW). The resonant frequency of the FBARs is determined by the thickness of the deposited piezoelectric layer and can therefore lie in a range from 500 MHz to far in excess of 10 GHz. The total reflection of the upper side occurs through an impedance jump at the transition from the upper electrode to the ambience (air or vacuum). For the total reflection on the lower side two techniques were developed: the reflection to ambience (air or vacuum), so-called Membrane-Type FBARs [*Solidly Mounted Resonators and Filters*, K. M. Lakin, K. T. McCarron, R. E. Rose, IEEE Ultrasonic Symposium, 905-908 (1995)] or to a buried acoustic Bragg grating, so-called Solidly-Mounted Bulk Acoustic Resonators (SBAR) [*Layered piezoelectric resonators with an arbitrary number of electrodes (general one-dimensional treatment)*, H. Nowotny, E. Benesk, M. Schmid, J. Acoustic Soc. Am., vol 3, 1238-1245 (1991), or *Face-mounted piezoelectric resonators*, W. E. Newell, Proceedings of the IEEE, vol. 53, 575-581, (1965)].

The technology of FBAR and SBAR components was optimised with reference to the requirements of the mobile telecommunications technology. These requirements, however, vary in important aspects with regards to the requirements of a mass sensitive resonator. Indeed, for both, a high quality factor is essential, however, a higher electro-mechanical coefficient of coupling is only required for filter applications. This high coupling coefficient was essentially used with longitudinally polarized wave types on ZincOxide (ZnO) or AluminiumNitride (AlN)-based piezoelectric layers. However, for mass sensitive applications of FBARs and SBARs in fluid environments (such as water, blood or oil) transversally polarized wave types are compulsory in order to ensure high quality. Longitudinal wave types couple too strongly to the fluid ambient, whereupon the quality factor sharply falls [see e. g. *First results on label-free detection of DNA and protein molecules using a novel integrated sensor technology based on gravimetric detection principles*, R. Gabl, H.-D. Feucht, H. Zeininger, et al., Biosensors and bioelectronics 19, 615-620 (2004)]. For this reason longitudinally oscillating FBARs and SBARs are only applicable for gas sensor applications.

Nearly all published works until now in the area of sensory applications of FBARs and SBARs are on this subject. Already in the mid 1970s K. M. Lang was able to produce and characterize the corresponding layers for transversally polarized wave types. These early works were not followed up, because the application for filter components due to the properties of shear waves was not considered relevant for filter applications. New works try henceforth, with the use of apertures within the layer growth of the standard FBAR and SBAR processes of the filter technology, to tilt the axis of polarization and to therefore allow the excitation of transverse polarized waves [*Novel Integrated FBAR sensors: a universal technology platform for bio- and gas-detection*, R. Gabl, E. Green, M. Schreiter, H. Feucht; H. Zeininger, R. Primig, D. Pitzer, G. Eckstein, W. Wersing, Proceedings of IEEE, Vol. 2, 1184-1188 (2003)]. Therefore however the tilt of the polarization axis varies, dependant upon its position across the whole wafer surface. This process is therefore not appropriate for bulk production.

With respect to the piezoelectric material ZnO, in recent years K. M Lakin's preliminary works have been taken up again [*Thin Film Resonator Technology*, K. M. Lakin—IEEE transactions on Ultrasonics, Ferroelectrics, and Frequency Control, vol. 52, no. 5, 707-716 (2005); or *Solidly Mounted Resonators and Filters*, K. M. Lakin, K. T. McCarron, R. E. Rose, IEEE Ultrasonic Symposium, 905-908 (1995)] and in the meantime a growth process has been developed for the (11-20) texturised ZnO, which allows the excitation of transversally polarized waves. However, the acoustic properties of ZnO for mass sensitive applications are clearly inferior with respect to GaN. The acoustic velocity of the transversal polarized wave in (11-20) GaN is namely 4294 m/s [*Mass Sensitive Thin Film Bulk Acoustic Wave Resonators*, M. T. Loschonsky, D. Eisele, L. M. Reindl, IEEE International Frequency Control Symposium (2006)] which is higher than that of (11-20) ZnO, which is 2730 m/s [*Electromechanical Coupling Coefficient k15 of (1120) Textured ZnO Films*, T. Yangitani, N. Mishima, M. Matsukawa, Y. Watanabe, IEEE Ultrasonics Symposium 2005].

Thereby with equivalent layer thicknesses, with GaN a higher resonant frequency and therewith a higher mass sensitivity is achieved. Furthermore, with GaN-based resonators, one expects a higher quality factor than with those based upon ZnO, whereby the measurement noise is reduced.

The piezoelectric material Paratellurite, discovered in 1964, displays the exceptional property that only transversally polarized waves can be excited. The use of this material is problematic, due to its cell damaging properties, and thus it would be very difficult to use it within the areas of medicine or biology.

In the meantime GaN and the therewith associated AlN have attained large commercial importance within the optoelectronic and electronic areas. In the area of BAW applications one works partly with sputtered AlN layers [*Low temperature AlN thin films growth for layered structure saw and baw devices*, M. B. Assouar, O. Elmazria, M. El. Hakiki, P. Alnot, C. Tiusan, IEEE International Symposium on Applications of Ferroelectrics, 43 (2005)] and one works more rarely with epitaxial layers. In recent years such epitactic c-planar AlN- and GaN-BAW layers have been investigated by many groups, whereby these investigations prove the excellent suitability of these materials for BAW components [*Realization of waveguiding epitaxial GaN layers on Si by low-pressure metalorganic vapor phase epitaxy*, H. P. D. Schenk, E. Feltin, M. Laügt, O. Tottereau, P. Vennégues, E. Doghèche, Applied Physics Letter 83, 5139 (2003); *High frequency SAW devices on AlGaN: Fabrication, characterization and integration with optoelectronics*, T. Palacios, F. Calle, J. Grajal, E. Monroy, M. Eickhoff, O. Ambacher, F. Omnès, Proceedings of the IEEE Ultrasonics Symposium 1, 57 (2002); or *Epitaxially grown GaN thin-film SAW filter with high velocity and low insertion loss*, S.-H. Lee, H.-H. Jeong, S.-B. Bae, H.-C. Choi, J.-H. Lee, Y.-H. Lee, IEEE Transactions on Electron Devices, 48, 524 (2001)]. Thereby, the propagation direction of surface acoustic waves in c-planar GaN is always perpendicular to the substrate upper surface. It is very different with a-planar (11-20) GaN, in which the propagation direction lies planar. Such a-planar GaN is currently the preferred material in optoelectronics, because with in-plane piezo fields one can expect an improved efficiency from light emitters. However, currently, in comparison to c-planar GaN, the material quality is relatively bad. This is due to the more demanding growth procedure of a-planar GaN, as the material, and in particular also AlN, shows a preference towards c-planar orientation and these dislocations are not so easy to annihilate. On r-planar sapphire it is however relatively easy to grow a-planar GaN, although with a tolerable morphology, i. e. a relatively rough upper surface.

Hence the problem underlying the present invention is to provide an improved piezoelectric sensor arrangement, which exhibits a higher sensitivity and reproducibility and, at the same time, is easy and cheap to produce.

This problem is solved with the subject of the independent claim 1. The advantageous further embodiments of the present invention are the subject of several dependent claims.

The present invention is based upon the idea to produce and optimize piezoelectric sensor arrangements, in particular for the application in fluids with a mass resolution in the femtogram range, as for example mass sensitive thin film shear wave resonators built according to the acoustic Bragg grating principle by usage of epitaxial deposition techniques such as metalorganic vapour phase epitaxy (MOVPE), grown transversal polarized piezoelectric group III Nitride layers, such as GaN or AlN or Ga1-x-yAlxInyN-layers with $0 \leq x \geq 1$ and $0 \leq y \geq 1$.

As an alternative to MOVPE, molecular beam epitaxy (MBE), hydride vapour phase epitaxy (HVPE) or chemical vapor deposition (CVD) can also be used.

A mass sensitive sensor system for process technology and medical-chemical-biology applications can be put into effect, according to a beneficial embodiment, based upon the present invention sensor arrangement.

In particular, at the same time, the suitability for mass production of all the processes used to produce micro system technology sensor arrays with different selectively sensitive layers is advantageous. The advantageous layers, which are achieved with the present invention process, are also of great interest for the growth of GaN light emitters on nonpolar surfaces as well as for application within the low-cost light emitters market, in the case of the growth on metalized silicon surfaces.

According to an advantageous embodiment, SBARs are used for mass sensitive applications with a resolution of less than 1 picogram. Indeed according to the innovation one can also use these principles both for membrane-based FBARs and also for acoustic bragg grating-based SBARs.

For the application as a biological or chemical sensor, the attachment of the to be detected analyte molecules to the chemical-biological sensitive layers will be used to change the resonant characteristics of the SBARs. Through the additional analysis of the higher frequency modes with different thermal responses, in an effective method one can achieve a simultaneous compensation of the thermal response. The sensitive layers can therefore be superimposed onto the sensitive area of the sensor arrangement, according to a differing but known method, e. g. according to the so-called Top-Spot-Method [*TopSpot—a new method for the fabrication of Microarrays*, J. Ducrée, H. Gruhler, N. Hey, M. Müller, S. Bekesi, M. Freygang, H. Sandmaier, R. Zengerle, Proc. of IEEE-Conference on Micro Electro Mechanical Systems MEMS 2000, Miyazaki, Japan, 23-27. Jan. 2000; p. 317-322 (2000); or *Highly Parallel Dispensing of Chemical and Biological Reagents*, B. de Heij, M. Daub, 0. Gutmann, R. Niekrawietz, H. Sandmaier, R. Zengerle, Analytical and Bioanalytical Chemistry; Vol. 378, 119-122 (2004)]. In particular thereby complex sensor arrays can also be produced in a simple manner.

In general, different layers and subsequent layers for thin film shear wave resonators can be made, according to the present invention, with the help of epitaxial processes such as metalorganic vapour phase epitaxy (MOVPE), molecular-beam epitaxy (MBE), and hydride vapour phase epitaxy (HVPE). This also relates in particular to group III Nitride-based component layers. For example very good oriented a-planar GaN can be made with a half-width of co-scan of the (11-20) reflex of 1000 arcsec and with a smooth morphology, apart from a few scratches. Furthermore MOVPE growth of a-planar AlN can be used to produce piezoelectrical sensor arrangements. AlN has an even stronger tendency to c-planar oriented growth than GaN, whereby the a-planar AlN growth will come more into demand.

BRIEF DESCRIPTION OF THE DRAWINGS

On the basis of the described advantageous embodiment in the enclosed drawings, the invention will be discussed in more detail in the following. Similar or corresponding particulars of the inventive embodiments are annotated with the same reference numerals. The Figures show.

DETAILED DESCRIPTION OF THE DRAWINGS

Figures 1, 2:
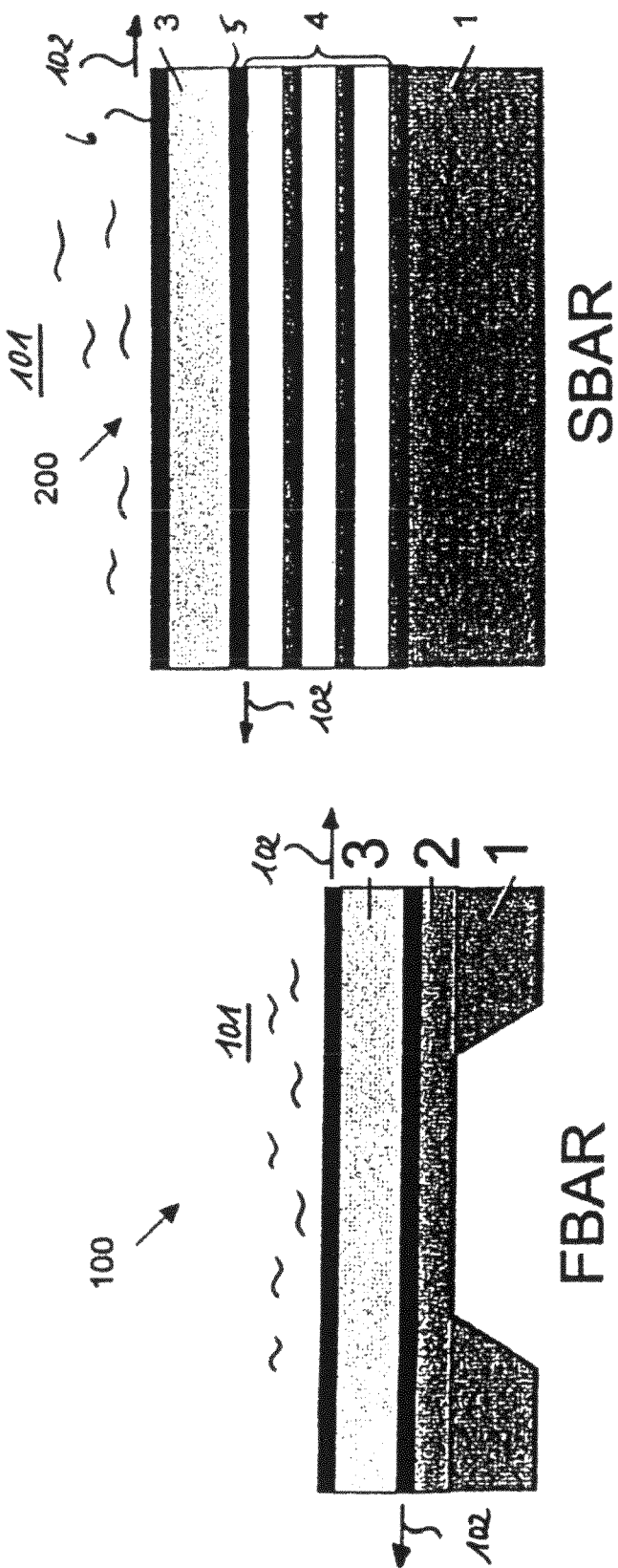
FIG. 1 A schematic representation of a piezoelectric sensor arrangement according to a first advantageous embodiment.
FIG. 2 A schematic representation of a piezoelectric sensor arrangement according to a second advantageous embodiment.

FIG. 1 schematically shows a piezoelectric sensor arrangement 100 according to the above-described membrane-type FBAR-principle, wherein a carrier membrane 2 is arranged on a substrate 1. The carrier membrane 2 holds on one side the piezoelectric layer 3 which is embedded between two electrodes 5,6 and on the opposite side is connected to air or vacuum through an opening in the substrate. A sensitive area of the sensor arrangement 100 is connected with a measurement fluid 101 which can be either a liquid or a gaseous measurement medium. Depending on the application a sensitive layer is placed on the top electrode 6 of the piezoelectric layer 3. Analyte molecules, which need to be detected, attach themselves there and cause a shift of the resonance frequency due to the increased mass. On the other hand, the uncoated sensor arrangement can also be used for direct analysis of mechanical and elastic properties, such as the viscosity, of a measuring fluid.

The arrow 102 symbolizes thereby the transversally polarized oscillation of the thin film resonator.

As an alternative, the SBAR sensor arrangement 200 in FIG. 2 comprises a buried acoustic Bragg grating 4.

According to an advantageous further embodiment of the present invention, the minimizing of the thermal response is achieved through the excitation of two different modes with differing thermal responses for a mathematical compensation of the thermal cross-effect.

These thermally responsive thin film resonators which compensate the thermal response, are built into a low-noise, long-time stable oscillator circuit as gravimetric sensors, and subsequently integrated into a process suitable micro system technology overall system.

Some parameters of a possible system are listed in the following:

Oscillating resonator mass: 7 ng
Resonant frequency: 1.88 GHz,
SNR 20 dB
Number of measuring points for an evaluating interval: N=2500 when tA=1 s For the so-called Cramer-Rao-Lower-Bound (CRLB) in combination with (1), this therefore leads to the following:

$$\mathrm{var}(f_0) \geq \frac{6}{4\pi 100 * 2500 * (2500^2 - 1)}$$

$$\frac{\Delta f}{f} = 3.056E - 13$$

$$\Delta m = 21.392 - 22g$$

The highest accuracy is achieved when, according to the advantageous further embodiment of the present invention, the acoustic thin film resonator is simultaneously used as a temperature sensor. This is achieved through the use of two or more resonant modes with distinctly different thermal responses. Furthermore, for a compensation of the thermal responses opposing stresses of the Al(Ga)N/Ga(Al,In)N-layers are used.

The MOVPE growth of GaN-based Bragg reflectors is well-known for optical applications, but not for acoustic applications. The growth of such acoustic Bragg reflectors on Si is not viable, due to the required large layer thicknesses and the minor differences in the acoustic refractive index of the material types, as this inevitably leads to ruptures of the layers. Sputtered reflectors are more suited for it, whereby as an example W—SiO$_2$ subsequently alternating layers can be sputtered which then have amorphous and polycrystalline structure, respectively. However, in contrast to the usual sputtered materials from single crystals respectively strongly textured materials, there will be less damping of the reflectors and therefore a better quality factor is expected. The is described, for example, for sputtered metals and oxides as well as nitride layers in *Texturing effects in molybdenum and aluminium nitride films correlated to energetic bombardment during sputter deposition*, T. P. Drüsedau, K. Koppenhagen, J. Bläsing, R.-M. John, Applied Physics A: Materials Science & Processing 72, 541 (2001).

According to a possible manufacturing method a sputterer is used for depositing these acoustic reflector layers are onto an appropriate metal layer and then in conclusion either a c-planar or a-planar GaN or AlN will be grown. As preferred surfaces a-, m- and r-planar surfaces are named. The growth of r-planar GaN is described by way of example in *Influence of buffer layers on MOVPE grown GaN on Si* (001), F. Schulze, J. Bläsing, A. Dadgar, and A. Krost, Appl. Phys. Lett. 84, 4747 (2004) and *GaN heteroepitaxy on Si* (001), F. Schulze, A. Dadgar, J. Biasing, and A. Krost, Journal of Crystal Growth 272, 496 (2004). The m-planar surface is significantly more difficult to grow, and to date there is the possibility to grow this, amongst others, on a-planar Sapphire. With all of these preferred surfaces, a misorientation to the surface normal of ±5° and also beyond is tolerated, whereby above 5° the quality of the component decreases dramatically with increasing misorientation. In literature up until now HfN is known as the only metal or highly conductive material upon Silicon on which high quality GaN can be grown [*Lattice-matched HfN buffer layers for epitaxy of GaN on Si*, R. Armitage, Qing Yang, H. Feick, J. Gebauer, Satoko Shinkai, Katsutaka Sasaki and E. R. Weber, Applied Physics Letters 81, 1450 (2002)].

Experiments with pure metals (Au, W, Mo, Ni, Pt) which were brought directly in contact with Si with electron beam physical vapor deposition (which, in opposition to sputter methods, mainly causes a reduced orientation of the layers) have shown Ni to be a suitable metallization material. This gives the opportunity for a combined production of SBAR structures using sputter- and epitaxial methods.

The present invention enables the development of a mobile measuring system, with a novel basis, according to the acoustic Bragg grating principle assembled mass sensitive thin film shear wave resonators with a mass resolution in the femtogram area and within which those can also be operated in a fluid measuring environment. To this end, optimized piezoelectric layers come into use, which are especially for the excitement of the transversal polarized waves.

Further fields of application such as process technology, food technology and safety engineering can be covered according to the development with further specific selectively-sensitive layers.

According to the present invention, the technological production of the thin film shear wave resonators is improved thus, that the resonators are also guaranteed to be eligible as sensors for mass detection in a fluid measuring environment.

Gravimetric sensors for selective biochemical applications can be built and integrated into a mobile micro system technology-based complete system, based upon such piezoelectric sensor arrangements. Special micro system technological technologies facilitate the development of complex sensor arrays including low-noise oscillators and an evaluation unit.

Subsequently an example of a possible production process for group III Nitride-based transversally polarized piezoelectric layers is described.

A controlled growth process for high quality a-planar GaN layers on r-planar Sapphire with (11-20)- and (1-102)-X-ray half widths in the ω domain of less than 500 arcsec, as well as for single crystal a-planar AlN- and AlGaN-layers, must fulfill strict requirements, because contrary to the growth of c-planar GaN, the growth of a-planar GaN exhibits significant differences. A lower dislocation density and good surface morphology, both of which are indispensible for a fully functioning component, cannot be achieved with methods known for c-planar GaN. On the one hand, this is due to the difference in the growth rates in the c-axis direction and perpendicular to this, and, on the other hand, due to the complicated annihilation of perpendicularly-oriented dislocations with a-planar GaN. Complex methods such as epitaxial lateral overgrowth, which is hardly at all used with c-planar GaN, are experiencing a renaissance. Contrary to such approaches, according to the present invention, the layers are preferably deposited with simple methods, such as the use of in-situ SiN masking layers in order to achieve a significantly reduced slip and thereby to improve the material. For this the exact knowledge of the best growth conditions for the preferred lateral growth of a-planar GAN is necessary. The growth of high quality aluminum-containing a-planar layers and respectively of AlN on GaN, or directly onto the substrate, is hindered due to the tendency of higher order qualitative high temperature AlN to orient in the c-axis, such that, as an alternative, a thin interlayer can be designed.

The following enters into more detail for the choice of the designated materials for the electrodes, the Bragg grating layers and the substrate (Si, Sapphire, technical glasses). A complete SBAR 200, which is depicted in FIG. 2, consists primarily of five parts:

Substrate 1
Acoustic Bragg grating 4
Lower electrode 5
Piezoelectric resonator layer 3
Upper electrode 6

With all five parts, process relevant and acoustic material properties should be considered. For substrate 1, it is essential that, along with the requirements for high acoustic impedance and a high modulus of elasticity, there is also good process manageability, in particular for the further stages of assembly and bonding technology and packaging. The acoustic Bragg grating 4 comprises a sequence of two layers with different acoustic reflection and transmission coefficients. The crucial part in this is the material density, the crystal lattice structure and the crystal orientation of every single layer. The layer growth of GaN, AlN; AlGaN; AlGaInN, and group III Nitride layers in general, on metal surfaces and on substrates is therefore to be optimized for bond strength, acoustic transmission and reflections. For this the properties relating to the following epitaxial growth of high quality GaN or AlN films or group III Nitride films should also be considered.

The differing layers should be characterized individually and in their interrelations with each other. The following parameters are thereby essentially important:

Elastic constant
Acoustic phase- and group velocity
Acoustic damping
Electro-mechanical coupling constants of the piezoelectric layer
Dielectric constant
Temperature dependencies of the material constants
Effect of the crystal dislocations and defects as well as diffusion effects at layer transitions From these material properties a one dimensional model of the shear wave resonator can be designed. The outcome of this is:

The impedance situation from the electrode geometry
The quality factor from the material parameters
The bandwidth from the layer strata of the Bragg reflector
The resonant frequency from the layer thickness of the piezolayer and the Bragg reflector
The insertion loss from the material parameters taking the layer order into consideration The excitation and frequency characteristic of the higher modes and the parasitic neighbouring modes arise due to the existence of rotational symmetry from a 2D model, apart from that of a 3D model. These parameters and the acoustic mode profiles are calculated from these models, which determine the subsequent damping in the fluid medium.

Thus the layer order can be optimized according to the following principles:

Maximum quality factor, minimal damping
Minimal thermal response
Maximum sensitivity
Additional strong excitation of a minimum of one neighbouring mode with its own thermal response and a different mass sensitive as reference, alternatively an additional temperature sensor could be integrated into the chip
Suppression of all other neighbouring modes According to the present invention a piezoelectric sensor arrangement can furthermore be built from a matrix of SBARs with different selectively sensitive layers for multi-component analysis. To this a multiplicity of resonators can be built up in an acoustic and electromagnetically decoupled arrangement, coated with micromechanical fabrication technology (such as the so-called Top Spot method). There follows the subsequent integration into a mobile measuring system with a control and readout unit.

The present invention piezoelectric sensor arrangement can also be used in a beneficial manner for a viscosity sensor within the automobile industry, for example for mineral oil. Thereby the viscosity of the oil will be detected through evaluation of the resonant frequency of the sensor arrangement, viscosity is here a measure of the ageing condition of the oil.

Although until now only application examples have been elaborated upon whereby the present invention of the piezoelectric sensor arrangement is depicted in a liquid measuring material, the measuring fluid can of course also be in a gaseous form. With the help of special sensitive coatings, a monitoring of these gases regarding different chemical or biological agents can be performed.

What is claimed is:

1. Piezoelectric sensor arrangement for the operation in a measuring medium, wherein the sensor arrangement comprises an acoustic resonator with a sensitive area, which is arranged such that a resonant frequency of the sensor arrangement can change in response to one or more properties of the measuring medium,
wherein the acoustic resonator comprises a piezoelectric thin film resonator, and wherein a piezoelectric layer of the film resonator comprises a group III Nitride layer with an orientation differing from the c-axis and is epitaxially fabricated in a way that transversally polarized oscillation modes are excited during a measurement, and
wherein the acoustic resonator is designed such that a minimum of two oscillation modes with differing frequencies and differing thermal responses are excited during the measurement in order to calculate the compensation for the thermal response of the piezoelectric sensor arrangement.

2. Piezoelectric sensor arrangement according to claim 1, wherein the piezoelectric layer comprises a Gallium Nitride layer.

3. Piezoelectric sensor arrangement according to claim 1, wherein the piezoelectric layer comprises an Aluminium Nitride layer.

4. Piezoelectric sensor arrangement according to claim 1, wherein the piezoelectric layer comprises a Al(1-x)Gax-Nitride layer, where $0 \leq x \leq 1$.

5. Piezoelectric sensor arrangement according to claim 1, wherein the piezoelectric layer comprises a Al(1-x-y)Gax-Iny-Nitride layer, where $0 \leq x \leq 1$ and $0 \leq y \leq 1$.

6. Piezoelectric sensor arrangement according to claim 1, wherein the piezoelectric thin film resonator has a membrane-type design with an acoustic total reflection on the backside of the piezoelectric sensor arrangement.

7. Piezoelectric sensor arrangement according to claim 1, wherein the piezoelectric thin film resonator comprises a buried acoustic Bragg reflector which is designed for total reflection on the backside of the piezoelectric sensor arrangement.

8. Piezoelectric sensor arrangement according to claim 1, wherein the acoustic resonator contains a sensitive area which is composed from a selective, reversible binding detection layer for the measuring of an analyte within the measuring medium, wherein the presence and/or the concentration of the analyte is detected with a frequency change due to the absorption of the analyte.

9. Piezoelectric sensor arrangement according to claim 1, wherein the acoustic resonator has a sensitive area, which is implemented such that the elastic properties of the measuring medium are detected through the change in the resonant frequency of the thin film resonator.

10. Piezoelectric sensor arrangement according to claim 9, wherein the measuring medium is a mineral oil in an automobile and the detecting elastic property is the viscosity of the oil.

11. Piezoelectric sensor arrangement according to claim 1, which is operated in a gaseous measuring medium.

12. Piezoelectric sensor arrangement according to claim 1, which is operated in a liquid measuring medium.

* * * * *